United States Patent
Cummings et al.

[11] Patent Number: 6,093,407
[45] Date of Patent: Jul. 25, 2000

[54] ANTI-MICROBIAL POWDER COATINGS

[75] Inventors: Frederick L. Cummings, Richmond; Peter Gottschling, Friendswood; Jeffrey R. Hagerlin, Houston, all of Tex.

[73] Assignee: DuPont Powder Coatings USA, Inc., Houston, Tex.

[21] Appl. No.: 09/165,839

[22] Filed: Oct. 2, 1998

Related U.S. Application Data

[60] Provisional application No. 60/061,099, Oct. 3, 1997.
[51] Int. Cl.[7] .............................. A61K 9/00; A61K 9/14; A01N 25/00
[52] U.S. Cl. .......................... 424/400; 424/405; 424/489; 514/951
[58] Field of Search .................................... 424/400, 405, 424/489; 514/951

[56] References Cited

U.S. PATENT DOCUMENTS

| | | | |
|---|---|---|---|
| 3,817,761 | 6/1974 | Brake | 106/18.32 |
| 4,629,645 | 12/1986 | Inoue | 428/141 |
| 5,238,749 | 8/1993 | Cueman et al. | 428/441 |
| 5,980,620 | 11/1999 | Brodie et al. | 106/15.05 |

OTHER PUBLICATIONS

BioCote, "Test Certificate" University of Wolverhampton (May 1997).
Silikal Resin Systems, *"Unique Flooring Systems with Microban Antimicrobial Protection"* pp. 1–8, (Aug. 1997).

*Primary Examiner*—Kevin E. Weddington
*Attorney, Agent, or Firm*—Trop, Pruner & Hu, P.C.

[57] ABSTRACT

Improved powder coatings exhibit enhanced resistance to bacterial and fungal attack, while possessing excellent toughness, appearance, corrosion resistance, durability, processability, and ease of application. The coating is comprised of anti-microbial agents melt-processed into the matrices of powder coatings. An article may be coated with a thermoset or thermoplastic powder which may be applied by electrostatic spray, by dipping it into a fluidized bed (or electrostatically charging it and then dipping it into the fluidized bed), or by thermal or flame spray.

16 Claims, 1 Drawing Sheet

ANTI-MICROBIAL POWDER COATINGS

This application is based on provisional application Ser. No. 60/061,099, filed on Oct. 3, 1997.

BACKGROUND

This invention relates generally to powder coatings and particularly to anti-microbial powder coatings.

Public concern about the health hazards arising from microorganisms such as bacteria, fungi, viruses and the like is high. Many people are concerned that contact with objects in public facilities may result in illness. Also, it is desirable to prevent biological defacement of object surfaces due to the growth of microorganisms.

Thus, a number of efforts have been undertaken to produce objects with the ability to kill or inhibit the growth or reproduction of microorganisms, which is termed "anti-microbial activity" herein. For example, plastic materials with anti-microbial activity are known. The resulting plastic products then exhibit some degree of anti-microbial activity.

For example, some toys for young children include anti-microbial agents (i.e., agents with anti-microbial activity) within a plastic matrix. These anti-microbial agents, which are believed to be safe, are believed to inhibit the growth of various microorganisms. Anti-microbial agents in the final coatings including paint and powder coatings are known. However, none of the existing techniques in powder coatings have gained substantial acceptance.

Therefore, there is a continuing need for improved coatings and particularly for improved powder coatings that exhibit anti-microbial activity when applied to substrates.

SUMMARY

An anti-microbial powder coating composition includes an anti-microbial agent homogeneously dispersed within particles of a resin-based powder.

DETAILED DESCRIPTION

Figure 1:
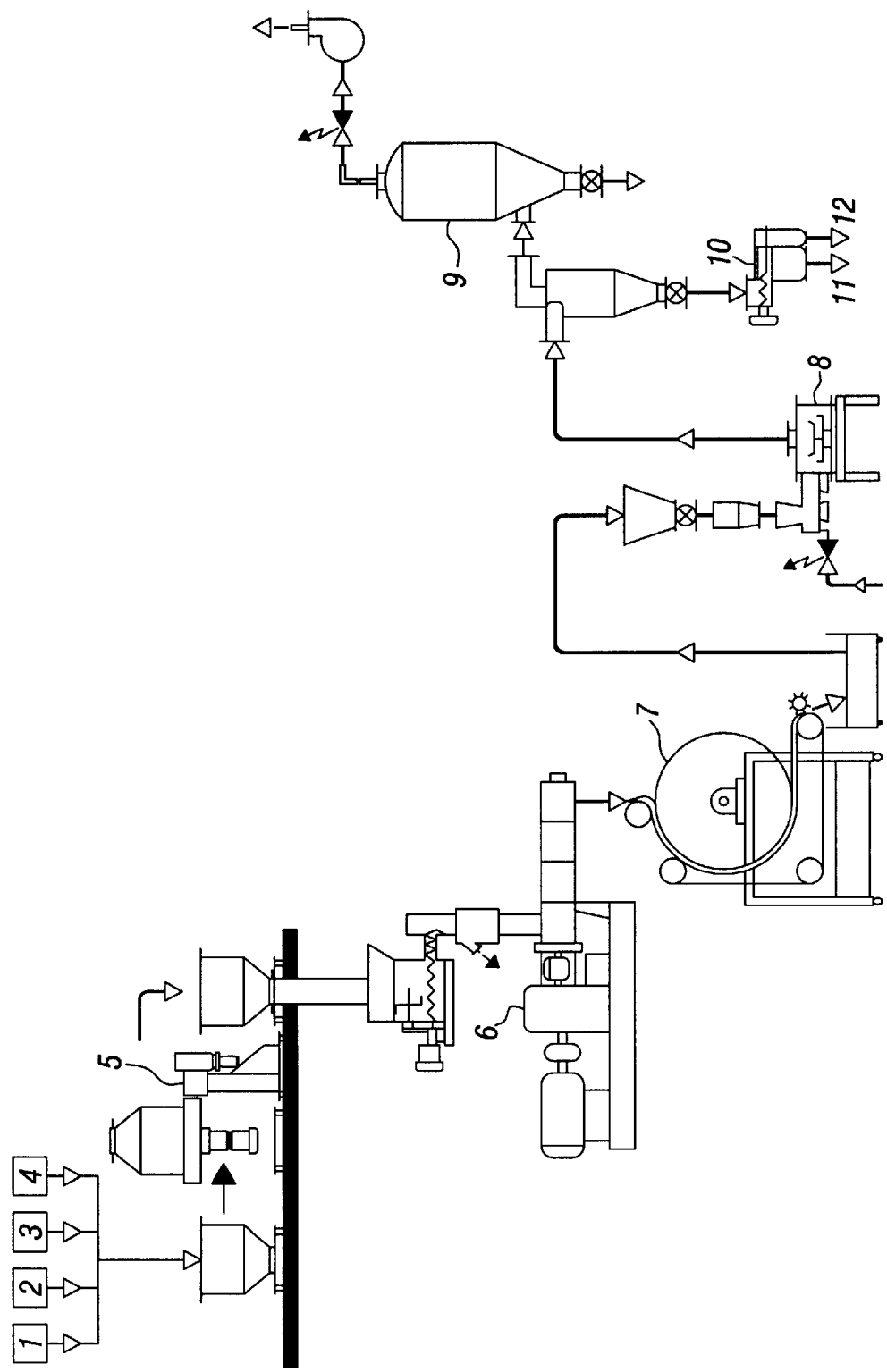
FIG. 1 is a diagrammatic depiction of a process for making a powder coating.

A stable anti-microbial powder coating composition may coat a product that may be exposed to bacteria and fungal spores. The powder coating may be made by a process that produces a homogeneous distribution of anti-microbial agents that may promote consistent and efficient anti-microbial activity. Once coated with the anti-microbial powder coating, a substrate may be protected from physical abuse by the film's physical properties and durability and from degradation due to attack by microorganisms and also potentially protecting the user from various microorganisms.

The powder coating formulation may be applied to the substrate so that bacterial or fungal contact with the coating either kills them or at least inhibits their growth. For example, in some embodiments, anti-microbial activity with respect to *Staphylococcus aureus, Escherichia coli, Bacillus subtillus, Streptococcus faecadis, Salmonella typhinurium, Pseudomonas aeruginosa*, and other Gram positive and Gram negative bacteria may be achieved. Powder coating formulations, in some embodiments, may also inhibit the growth of certain higher organisms like algae, fungi, filamentous fungi (Aspergillus, Aureobasidium, Botrytis, Ceratostomella, Cuvularia, Fusarium and Penicillium species), yeast and also, some viruses.

Potential applications for these improved powder coatings may include, for example, food preparation areas, restrooms, hospitals, garbage disposals, stockyard areas, animal feed troughs, schools, kitchens, swimming pool areas, dishwashers, automobile fixtures, public access fixtures, public seating, public transportation fixtures, toys, and other industrial, agricultural, commercial or consumer products.

The resin may be one or more of the thermosetting and/or thermoplastic resins including those based on epoxy, polyester, acrylate and/or polyurethane resins. The coating may also include from about 0.1 percent to about 10 percent by weight of the total composition of one or more non-reactive liquid or solid anti-microbial agents.

Examples of thermoplastic or thermosetting coatings that may be used, in addition to epoxy powder coatings, include saturated and unsaturated polyesters, acrylics, acrylates, polyester-urethanes, acrylic urethanes and hybrids such as epoxy-polyester, polyester-acrylic and epoxy-acrylic powder coatings. Thermoplastic powder coatings that may be useful include nylon, polyvinyl chloride (PVC), polyethylene, polyethylene terephthalate (PET), polybutylene terephthalate (PBT), and polypropylene as examples. These powder coatings may be cured or fused by thermal or photochemical methods.

The anti-microbial agents are preferably relatively non-reactive anti-microbial agents including phthalimides, acetamides, phthalonitriles, hydroxy benzoates, isothiazolinones, nitropropane diols, carbamates, methyl ureas, benzimidazoles, salicylanilides, mercury acetates, and organozinc compounds.

Non-reactive anti-microbial agents do not react with other compounds in the resin matrix to any significant extent. That is, they do not react to any degree that substantially affects their anti-microbial activity.

Among the liquid anti-microbial agents which are suitable in certain applications, a preferred anti-microbial agent is dibromocyanoacetamide (for example, Amerstat® 300 made by Drew Industrial Division of Ashland Chemicals, Boonton, N.J. 07005).

In addition, solid anti-microbial agents that are preferred include 2-bromo-2-nitropropane-1,3-diol (for example, Canguard® 409 made by Angus Chemical Co., Buffalo Grove, Ill. 60089) and 3,5-dimethyltetrahydro-1,3,5-2H-thiazine-2-thione (for example, Nuosept® S made by Creanova, Inc., Piscataway, N.J. 08855 or Troysan® 142 made by Troy Chemical Corp., West Hanover, N.J. 07936).

Other solid anti-microbial agents include N-(trichloromethyl)-thiophthalimide (for example, Fungitrol® 11 made by Creanova, Inc.), butyl-p-hydroxybenzoate (for example, Butyl Parabens® made by International Sourcing Inc., Upper Saddle River, N.J. 07458), diiodomethyl-p-tolysulfone (for example, Amical® WP made by Angus Chemical Co.), and tetrachloroisophthalonitrile (for example, Nuocide® 960 made by Creanova, Inc.).

The powder coating may be sprayed electrostatically onto a metal or nonmetal substrate. In this method, the substrate may be grounded. Charged particles of the powder coating are sprayed onto the substrate until a desired thickness is achieved. Other methods, such as fluidized bed coating methods or thermal or flame spraying, may also be used.

After the deposition is complete, the coated substrate is heated. For example, an electrical or gas fired oven may be used to cure or fuse the coating at temperatures in the range of 80° C. to 270° C. The curing time may be about five to twenty minutes for most substrates, but may vary from less than a minute to greater than one hour depending on the type of coating, the substrate, and the curing system. In addition to thermal methods, curing may also be achieved by electron beam or photochemical methods such as ultraviolet, infrared and the like. Curing of the coating can be effected by heat conduction, convection, radiation, or any combination of the three.

Advantageously, visible bubbling in the coating film after the curing process should be avoided. The presence of bubbles may indicate that some of the biocide may have been volatilized during the curing process. Advantageous anti-microbial agents should not produce visible bubbles indicative of volatilizing of the active element.

The powder coatings may be made by a melt extrusion method, as illustrated in FIG. 1. For example, a powder formulation includes more than one ingredient as represented by items 1–4. Fillers, extenders, flow additives, catalysts, hardeners, catalysts, pigments and other additives may be blended together with the resin and the anti-microbial agent in a premixer 5. The mixture may then be fed into an extruder 6 and heated to a temperature high enough to melt and mix the constituents. A temperature in the range of 50° C. to 150° C. may be sufficient. The molten extrudate may be immediately cooled by chill rolls 7 to form solid sheets.

The solid sheets may be further broken down to suitably sized chips. These chips are then fed into a grinder 8 which reduces the chips to fine particles. For example, particles having a mean particle size of about 10 microns to 100 microns are satisfactory. The resulting powder advantageously has a glass transition temperature that is greater than the storage temperature. A dust filter 9, a sieve screen 10, and powder inspection station 11 and 12 may also be provided.

The non-reactive anti-microbial agents are uniformly dispersed in the resin formulation (including the curing agent) during the premix stage. This is advantageous because there is no requirement that the anti-microbial agents have a specific particle size or particle size distribution. The anti-microbial agents are chosen to survive the extrusion process and the subsequent curing process in sufficient concentration to exhibit an anti-microbial effect in the final coating. In addition, it is preferable that the anti-microbial agent does not adversely change any important property of the final coating such as color.

Solid, non-reactive anti-microbial agents may be premixed directly with the formulation components. Alternatively, the particles of a solid anti-microbial agent may be bound with powder coating particles using impact fusion. With either method, mixing the anti-microbial particles with coating particles of the same particle size distribution is not necessary.

Liquid, non-reactive anti-microbial agents can be mixed readily with other components in the premix prior to extrusion. Liquid non-reactive anti-microbial agents often are difficult to dry blend into a powder to a concentration that consistently, effectively protects against bacteria or fungi. Alternatively, liquid anti-microbial agents may be mixed initially with particles of a solid support material such as a silica, clay or other resins in a masterbatch. The dry mixture containing the liquid anti-microbial agent may then be mixed into a formulation of resin.

For example, the liquid anti-microbial agent may be mixed at room temperature using high shear into fumed silica yielding high concentrations of active ingredients. The resulting granular solid may then be treated as a solid anti-microbial agent. For example, concentrations of approximately 66 percent of active ingredients in the fumed silica may be utilized.

Liquid and solid anti-microbial agents also may be incorporated within the powder coating particle by dissolving or mixing them and the other powder coating formulation components in a suitable solvent, e.g., organic liquids or supercritical fluids, and then removing the liquid in such a manner as to yield a powder or a solid product which can be processed into a powder.

A suitable powder coating material, which is utilized in the ensuing examples is Gold Bond III, a catalyzed epoxy powder coating sold by Herberts-O'Brien Inc., of Houston, Tex. Fillers and extenders, melt flow additives, dry flow additives, pigments and other additives may also be used to enhance specific physical properties, aesthetics, durability or other attributes.

EXAMPLE NO. 1.

A long-term anti-microbial activity test was carried out to determine if selected anti-microbial agents maintain their anti-microbial activity after being incorporated into powder coatings and cured.

Six anti-microbial agents were selected for experimentation. They are Fungitrol® 11, Amerstat® 300, Nuocide® 960, Nuosept® S, Propyl Parabens®, and Butyl Parabens®. For each powder coating formulation, one of the six anti-microbial agents was added at concentrations of 0.1 percent and 1 percent of the total resin weight.

Samples containing one of the six additives at the two concentrations in the coating matrix were prepared. The samples are coated on 2.54 cm. by 2.54 cm. by 0.08 cm. steel coupons. Both the front and the back of the coupons were coated with a given coating formulation. The edges were coated with a black silicone resin to prevent rusting of the coupon, which might interfere with the interpretation of the experimental results. Controls containing the coating formulation with no additive and controls containing only the black silicone resin used for edge coverage were included.

The target bacterial organisms were *Pseudomonas aeruginosa, Escherichia coli*, and *Salmonella typhinurium*. Five groups of samples were prepared. For each of the six additives, two panels with a coating thickness of 7 to 8 mils were cured with a normal schedule of 193° C. for 10 minutes. For each of the six additives, two panels with anti-microbial agent concentrations of 0.1 percent and 1 percent and with a coating thickness of 7 to 8 mils were cured with a normal schedule. Each of the following samples was prepared with an additive concentration of 1 percent of the resin by weight. For each of the six additives, two panels were prepared with a coating thickness of 3 to 4.5 mils and cured with a normal schedule.

The results were then rated on a scale of "0" (good performance) to "4" (poor performance) based on the number of colony-forming units observed. The growth ratings, which were averaged over the different samples, are based on the following numerical rating system:

0=No contamination (sterile).

1=Trace of contamination (1–9 colonies per "streak-inch").

2=Light contamination (10–99 colonies per "streak-inch").

3=Moderate contamination (greater than 100 colonies, but still distinguishable).

4=Heavy contamination (continuous smear of growth).

Resistance to fungal growth was tested generally in accordance with ASTM D5590-95. The organisms targeted were *Aspergillus niger* (ATCC 6275), *Penicillium funiculo-*

*sum* (ATCC 11797), and *Aureobasidium pullulans* (ATCC 9348) in a mixed spore suspension. Samples were aseptically placed onto a modified malt agar plate and then each sample was inoculated. The following data was determined after four weeks:

| ADDITIVE | AVERAGE BACTERIAL COVERAGE |
|---|---|
| CONTROLS | 3.0 ± 1.7 |
| FUNGITROL ® 11 | 2.8 ± 1.8 |
| PROPYL PARABENS ® | 3.7 ± 0.5 |
| BUTYL PARABENS ® | 2.6 ± 1.3 |
| AMERSTAT ® 300 | 1.6 ± 1.5 |
| NUOCIDE ® 960 | 3.0 ± 1.3 |
| NUOSEPT ® S | 3.6 ± 0.5 |

The Amerstat® 300 showed significantly improved bacterial coverage compared to the other additives and the control. The effect of decreasing the additive concentration was minimal. Decreasing the coating thickness had very little effect on the anti-microbial activity of the coating.

Among the tested additives, Propyl Parabens® and Nuosept® S did not appear to improve the activity relative to the control and thus it was concluded that little or no effect on the long-term anti-microbial properties given the chosen resin matrix.

The same samples were also exposed to fungus spores for a period of four weeks. Results of the study showed that several of the coatings showed no growth of fungi on is their surface after four weeks of exposure. At a concentration of 1 percent, powder coatings made with the Butyl and Propyl Parabens®, and Nuocide® 960 were free of visible fungal growth. Fungitrol® 11 and Amerstat® 300 had a very small amount of fungal growth. The Nuosept® S did not show conclusive fungal resistance.

An additional study was then undertaken using AATCC Test Method 30-1993, Part III. In this test, a control, Fungitrol® 11, Amerstat® 300, Nuocide® 960, Nuosept® S, Propyl Parabens® and Butyl Parabens® formulations were applied to steel coupons, as described previously. The samples were placed in sterile Petri dishes with Seboraud Dextrose Agar, inoculated with *Aspergillus niger*, (AATCC 6275), and incubated at 28° C. for three weeks. The fungus was placed on top of the coating as well as on the agar.

At the end of the three-week test period, only the control showed biological activity. When examined visibly and by microscope at one, two and three weeks, the control showed visible macroscopic fungal growth on its surface. The other formulations' surfaces did not have macroscopic or microscopic growth. Macroscopic growth was visible on the agar surfaces. However, it stopped at the coating edge. Since no zones of inhibition in the agar were visible, the anti-microbial agent is believed not to have leached out during exposure.

EXAMPLE 2

In order to determine how fast the anti-microbial agents are able to work, shorter-term tests were also conducted. In many applications, it is desirable that the anti-microbial agent operates quickly.

Steel coupons were coated with the Fungitrol® 11, Butyl Parabens®, and Amerstat® 300 anti-microbial formulations, at 0.1 percent and 1 percent, and exposed as per ASTM D 5588-94 to a mixture containing the bacteria *Pseudomonas aeruginosa, Staphylococcus aureus,* and *Escherichia coli.* After the coupons were washed with a 70 percent ethanol/water solution, they were placed in a sterile Petri dish, inoculated, and incubated at 32° C. for the duration of the test.

At appropriate intervals, each sample was checked for the presence of viable microorganisms by streaking each sample with a sterile cotton swab, then streaking the swab onto Tryptic Soy Agar. The plates were incubated for 48 hours at 32° C. The absence of microbial growth along the streak indicated that the corresponding sample did not contain viable microbial cells. The presence of microbial growth would indicate non-sterility, i.e., the sample contained viable microbial contamination.

The samples were examined for low levels of bacterial contamination by transferring an aliquot with a sterile cotton swab to a Tryptic Soy Broth in culture tubes. The tubes were incubated for 24 hours at 32° C., streaked onto Tryptic Soy Agar plates and the plates were incubated for 24 to 48 hours at 32° C.

Heavy bacterial growth was detected initially and after 4 hours for all samples; however, after 24 hours of exposure, differentiation in growth was visible among the samples. After 72 hours of incubation, the Butyl Parabens®-coated samples were free of bacterial growth and were actually sterile. The control showed low to heavy growth. The Amerstat® 300 and Fungitrol® 11 did not show conclusive results.

Next, steel coupons were coated with the anti-microbial formulations listed above and exposed per ASTM D 5588-94 to a mixture containing the fungus spores of *Aspergillus niger, Penicillium funiculosum,* and *Aerobasidium pullulans.* After the coupons were washed with a 70 percent ethanol/water solution, they were placed in a sterile Petri dish, inoculated, and incubated at 28° C. for the duration of the test. At appropriate intervals, each sample was checked for the presence of viable microorganisms by streaking each sample with a sterile cotton swab, then streaking the swab onto Potato Dextrose Agar (adjusted to pH 3.5 for fungi). These plates were also incubated at 28° C.

The absence of microbial growth along the streak indicated that the corresponding sample did not contain viable microbial cells. The presence of microbial growth would indicate non-sterility, i.e., the sample contained viable microbial contamination.

Heavy fungal growth was detected initially and after 4 hours for all samples. However, once again, at 24 hours of exposure, differentiation among the samples was observed. After 72 hours of incubation, Fungitrol® 11- and Butyl Parabens®-coated samples were free of (or showed very low levels of) bacterial growth.

EXAMPLE 3

Using AATCC Test Method 147 (Nutrient Broth, incubated at 37° C. for 18 to 24 hours), another test of very short term efficacy was undertaken. Cured powder coating formulations containing (0.1 percent and 1 percent) Fungitrol® 11, Amerstat® 300, Nuocide® 960, Nuosept® S, Propyl Parabens®, and Butyl Parabens® were exposed to a concentration of (inoculated) *Staphylococcus aureus, Escherichia coli,* and *Salmonella choleraesuis* for an exposure period of 18 to 24 hours. None of the formulations were effective in significantly killing the microorganisms over the short test cycle.

EXAMPLE 4

The next experiments were conducted, according to the procedure of Example 3, to evaluate the effect of higher anti-microbial concentration on short-term anti-microbial activity. Coating powders containing 2 percent Amerstat® 300, 4 percent Troysan® 174P, 5 percent Canguard® 409, 3 percent Irgasan® DP 400, 5 percent Amical® WP, 5 percent Nuosept® S, 10 percent Nuosept® S, 5 percent Nuocide® PCMC, and 10 percent Nuocide® PCMC were used in the next experiment.

Each formulation was loaded with anti-microbial agent until the powder became unstable. For example, if the powder sintered or cured too quickly, the concentration was reduced.

Significant zones of inhibition were achieved by the powder coatings containing 5 percent Canguard® 409, (bronopol), 3 percent Irgasan® DP 400 (triclosan, 5-chloro-2-(2,4 dichloro-phenoxy) phenol and 5 percent and 10 percent Nuosept® S. The bronopol (2-bromo-2-nitropropane-1,3-diol) formulation performed better than the triclosan formulation in inhibiting the growth of *Escherichia coli* and *Salmonella choleraesuis*.

The Nuosept® S performed as well as or better than the triclosan formulation in inhibiting the growth of *Escherichia coli* and *Salmonella choleraesuis*.

Thus, one preferred anti-microbial composition includes a mixture of anti-microbial agents that have short-term efficacy with agents having long-term efficacy. One preferred mixture includes 5 percent Nuosept® S and 0.1 percent Amerstat® 300 in a powder coating formulation.

What is claimed is:

1. An anti-microbial powder coating composition comprising an anti-microbial agent homogeneously dispersed within particles of a resin-based powder.

2. The composition of claim 1, wherein the powder coating composition comprises 90 to 99.9 percent by weight of one or more thermosetting and/or thermoplastic compositions based on epoxy, polyester, acrylate and/or polyurethane resins and 0.1 to 10 percent by weight of one or more anti-microbial agents.

3. The composition of claim 1 wherein said anti-microbial agent further comprises liquid anti-microbial agents.

4. The composition of claim 3, wherein the anti-microbial agent further comprises N-(trichloromethyl)-thiophthalimide.

5. The composition of claim 1 wherein the anti-microbial agent further includes 2-bromo-2-nitropropane-1,3-diol.

6. The composition of claim 5 wherein the 2-bromo-2-nitropropane-1,3-diol concentration is greater than 1 weight percent.

7. The composition of claim 6 wherein the 2-bromo-2-nitropropane-1,3-diol concentration is about 5 weight percent.

8. The composition of claim 1 wherein said anti-microbial agent further comprises solid anti-microbial agents.

9. The composition of claim 8 wherein the anti-microbial agent further comprises 3,5-dimethyltetrahydro-1,3,5-2H-thiazine-2-thione.

10. The composition of claim 9 wherein the 3,5-dimethyltetrahydro-1,3,5-2H-thiazine-2-thione concentration is greater than 1 weight percent.

11. The composition of claim 9 wherein the 3,5-dimethyltetrahydro-1,3,5-2H-thiazine-2-thione concentration is about 5 weight percent.

12. A method for preparing a anti-microbial powder coating composition comprising homogeneously mixing an anti-microbial agent into a powder coating pre-mix.

13. The method of claim 12, further comprising blending the components of the powder coating composition using a premixer, feeding the mixture into an extruder, and heating the mixture to a temperature high enough to melt it, cooling the melt, and processing the solid extrudate into a coating powder.

14. The method of claim 12, further comprising mixing liquid anti-microbial agents with particles of a solid support material and mixing said particles into the coating pre-mix.

15. The method of claim 13 further comprising treating the powder coating particles by impacting them with particles containing an anti-microbial agent to adhere the anti-microbial agent to the coating powder particles.

16. The method of claim 12 further comprising dissolving, dispersing or mixing the anti-microbial agent and the other components of the powder coating formulation into a liquid solvent, followed by removing the solvent in such a way as to yield a solid product which can be processed into a powder coating.

* * * * *

UNITED STATES PATENT AND TRADEMARK OFFICE
CERTIFICATE OF CORRECTION

PATENT NO. : 6,093,407
DATED : July 25, 2000
INVENTOR(S) : Frederick L. Cummings, Peter Gottschling and Jeffrey R. Hagerlin It is certified that error appears in the above-identified patent and that said Letters Patent is hereby corrected as shown below:

<u>Column 8,</u>
Line 2, please replace "includes" with -- comprises --.

Signed and Sealed this

Eighteenth Day of December, 2001

*Attest:*

*Attesting Officer*

JAMES E. ROGAN
*Director of the United States Patent and Trademark Office*